United States Patent [19]

Furukawa et al.

[11] 4,340,598

[45] Jul. 20, 1982

[54] HYPOTENSIVE IMIDAZOLE DERIVATIVES

[75] Inventors: Yoshiyasu Furukawa, Toyonaka; Shoji Kishimoto, Takarazuka; Kohei Nishikawa, Kyoto, all of Japan

[73] Assignee: Takeda Chemical Industries, Ltd., Osaka, Japan

[21] Appl. No.: 204,356

[22] Filed: Nov. 5, 1980

[30] Foreign Application Priority Data

Nov. 12, 1979 [JP] Japan .................... 54-146729

[51] Int. Cl.³ ............... A61K 31/415; C07D 233/64; C07D 233/90
[52] U.S. Cl. .................. 424/273 R; 548/337; 548/342; 548/343
[58] Field of Search ............... 548/342, 343, 337; 424/273 R

[56] References Cited

U.S. PATENT DOCUMENTS

| 2,946,804 | 7/1960 | Zaugg et al. | 548/342 |
| 3,354,173 | 11/1967 | Godefroi et al. | 548/343 |
| 3,932,445 | 1/1976 | Rasmussen | 548/342 |
| 4,038,286 | 7/1977 | Roevens et al. | 548/343 |
| 4,207,324 | 6/1980 | Matsumura et al. | 548/337 |

FOREIGN PATENT DOCUMENTS

| 50-84567 | 7/1975 | Japan | 548/342 |
| 1535566 | 3/1978 | United Kingdom . | |

OTHER PUBLICATIONS

Karppanen, Agents and Actions, 9:84–85, (1979).

Primary Examiner—Richard A. Schwartz
Attorney, Agent, or Firm—Wegner & Bretschneider

[57] ABSTRACT

Novel imidazole derivatives of the formula:

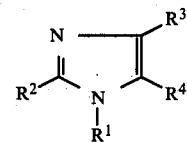

wherein
$R^1$ is lower alkyl or, phenyl-$C_{1-2}$alkyl which may be substituted with halogen or nitro;
$R^2$ is lower alkyl, cycloalkyl or, phenyl which may be substituted with halogen, lower alkyl, lower alkoxyl or di(lower alkyl)amino,
one of $R^3$ and $R^4$ is of the formula: $-(CH_2)_n-COR^5$ in the formula $R^5$ is amino, lower alkoxyl or hydroxyl and n is integer of 0, 1 or 2,
and the other is hydrogen or halogen;
provided that $R^1$ is lower alkyl or phenethyl when $R^3$ is halogen, n is 1 and $R^5$ is lower alkoxyl or hydroxyl, and their salts have hypotensive activity.

12 Claims, No Drawings

HYPOTENSIVE IMIDAZOLE DERIVATIVES

The present invention relates to novel imidazole derivatives which are of value as medicines and to their production and use. More particularly, the present invention provides compounds of the formula (I):

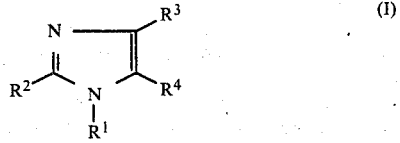

wherein $R^1$ is lower alkyl, or phenyl-$C_{1-2}$alkyl which may be substituted with halogen or nitro; $R^2$ is lower alkyl, cycloalkyl or, phenyl which may be substituted with halogen, lower alkyl, lower alkoxyl or di(lower alkyl)amino; one of $R^3$ and $R^4$ is of the formula: —$(CH_2)_n$—$COR^5$ in the formula $R^5$ is amino, lower alkoxyl or hydroxyl and n is integer of 0, 1 or 2, and the other is hydrogen or halogen; provided that $R^1$ is lower alkyl or phenethyl when $R^3$ is halogen, n is 1 and $R^5$ is lower alkoxyl or hydroxyl, and its salts which have the excellent angiotensin II antagonistic activity and hypotensive activity and are useful as a hypotensive agent.

Referring to the formula (I), lower alkyl as $R^1$ may be either straight-chain or branched, being preferably exemplified by alkyl having 1 to 6 carbon atoms such as methyl, ethyl, propyl, isopropyl, butyl, isobutyl, t-butyl, pentyl and hexyl; and preferred examples of phenyl-$C_{1-2}$alkyl include benzyl and phenethyl, which may for example have the substituent of halogen (e.g. chlorine and bromine) or nitro in the optional positions on their benzene rings.

Lower alkyl as $R^2$ may be either straight-chain or branched, being exemplified by methyl, ethyl, propyl, isopropyl, butyl, isobutyl, t-butyl, pentyl, hexyl, etc., and those having 1 to 6 carbon atoms are preferable; as examples of cycloalkyl there may be mentioned cyclopropyl, cyclobutyl, cyclopentyl and cyclohexyl, and those having 4 to 6 carbon atoms are particularly preferred. Halogen which are the substituents for the phenyl group as $R^2$ are preferably chlorine and bromine, while preferred example of lower alkyl in the lower alkyl, lower alkoxyl and di(lower alkyl)amino include those having 1 to 3 carbon atoms such as methyl, ethyl, propyl, and isopropyl. These substituents may locate in the optional positions on the benzene ring.

The halogen atoms as $R^3$ or $R^4$ are preferably chlorine or bromine, and preferred examples of lower alkoxyl as $R^5$ include alkoxyl having 1 to 3 carbon atoms such as methoxyl, ethoxyl and propoxyl.

In particular, the compound (I) when $R^3$ is hydrogen or $R^4$ is halogen with n in its counterpart, —$(CH_2)_n$—$COR^5$, being 1 is preferable.

The compound (I) can be produced in a high-yield, for example, by solvolyzing a compound of the formula(II):

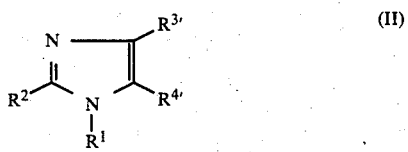

wherein $R^1$ and $R^2$ are as defined above; one of $R^{3'}$ and $R^{4'}$ is of the formula: —$(CH_2)_n$—CN in the formula n is integer of 0, 1 or 2, and the other is hydrogen or halogen. As the solvolysis, either method of hydrolysis and alcoholysis may be employed. Hydrolysis produces the compound (I) where $R^5$ is amino through the reaction with one mole of water or the compound (I) where $R^5$ is hydroxyl through the reaction with two moles of water, whereas alcoholysis affords the compound (I) where $R^5$ is alkoxyl corresponding to the alcohol employed. The hydrolysis is carried out by use of acid or alkali. Preferred examples of the acid include mineral acids such as hydrochloric acid and sulfuric acid. The concentration of such mineral acid in the reaction system is preferably 10 to 20% for hydrochloric acid and 40 to 60% for sulfuric acid, and in cases in which the compound (II) is less soluble in these acids, about 30 to 50% of acetic acid is advantageously allowed to coexist. As preferred examples of the alkali there may be mentioned alkali metal hydroxides such as sodium hydroxide and potassium hydroxide, and aqueous methanol and aqueous ethanol are advantageously employed as solvent. The hydrolysis reaction proceeds under heating. Normally, heating at 50° to 60° C. for 1 to 5 hours affords, as the main reaction product, the compound (I) where $R^5$ is amino, and further continued heating results in the compound (I) where $R^5$ is hydroxyl.

The alcoholysis is normally conducted by heating the compound (II) in alcohol corresponding to lower alkoxyl as $R^5$ with addition of acid, or then hydrolyzing, if necessary, an imino ether produced as an intermediate. Examples of such acid include hydrogen chloride, hydrogen bromide, p-toluenesulfonic acid, etc., which are used in the proportion of about 1 to 10 times the molar ratio of the compound (II). The reaction is preferably conducted under heating at about 50° to 100° C. for 1 to 10 hours. The resulting compound (I) where $R^5$ is lower alkoxyl can be derived, through hydrolysis, into the compound (I) where $R^5$ is hydroxyl, and, through reaction with ammonia, into the compound (I) where $R^5$ is amino group. The above-mentioned hydrolysis is desirably accomplished by reacting, with use of alkali metal hydroxide such as sodium hydroxide and potassium hydroxide, in a solvent such as aqueous methanol and aqueous ethanol at 20° to 100° C. for 5 to 10 hours. The reaction with ammonia, on the other hand, is preferably conducted by reacting with aqueous ammonia or ammonia-containing alcohol in a solvent such as methanol and ethanol at 20° to 50° C. for 5 to 50 hours. If necessary, the reaction can be carried out in a pressure vessel.

The compound (I') where Rhu 3 is hydrogen, n being 1 and $R^5$ is hydroxyl can be synthesized also by the following new reaction:

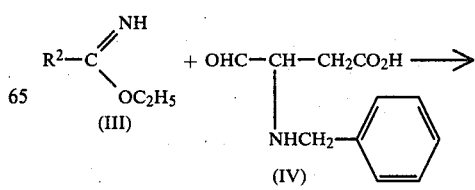

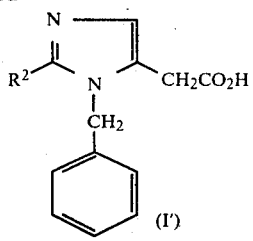

This reaction proceeds by heating at 50° to 120° C. for 1 to 5 hours while using dioxane, ethanol or their mixture as a solvent.

The resulting compound (I) where phenyl is present in $R^1$ can be subjected to nitration. The nitration proceeds by the conventional methods, such as the procedure of stirring in a mixture of glacial acetic acid and fuming nitric acid at 10° to 50° C. for 1 to 5 hours.

The resulting compound (I) where $R^5$ is hydroxyl group can be subjected to esterification to derive into the compound (I) where $R^5$ is alkoxyl. The esterification is carried out by the conventional procedures, e.g. by reacting in an alcohol corresponding to alkoxyl as $R^5$ in the presence of acid catalyst (e.g. sulfuric acid, hydrogen chloride, p-toluenesulfonic acid, etc.) at a temperature near the boiling point of the above-mentioned solvent for 1 to 5 hours.

The compound (I) produced in this manner can be easily isolated from the reaction solution by the conventional separation and purification procedures such as dilution with water, extraction, concentration, neutralization and recrystallization. These compounds (I) can be derived into pharmaceutically acceptable salts with acids or bases, such as salts with inorganic acids e.g. hydrochloride, sulfate and nitrate, salts with organic acids, e.g., depending upon type of the compounds, acetate, oxalate, succinate and maleate, salts with alkali metals e.g. sodium salt and potassium salt, and salts with alkaline earth metals e.g. calcium salt.

The compounds (I) prepared by the above procedure and their salts, being low in toxicity and suppressing the vasoconstrictive and blood-pressure elevating actions of angiotensin II, exhibit the excellent hypotensive activity toward animals, particularly mammals (e.g. dogs, rabbits, rats, men, etc.), and are of value as a treatment agent for hypertension. When one of the compounds is employed as such a hypotensive agent, the compound (I) or its salts as mentioned above can be orally or parenterally administered, either as such or in the form of powder, granule, tablet, capsule, injection, etc. prepared by mixing with a suitable, pharmaceutically acceptable carrier, vehicle and diluent. Though the quantity of the compound to be administered varied depending upon the kinds of diseases to be treated, symptoms, subjects and routes of administration, etc., it is preferably given in a daily dose of 10 to 100 mg for oral administration and 5 to 50 mg for intravenous injection, 2 to 3 times a day, in case of administration to adult humans as a treatment agent for essential hypertension.

The starting compounds (IIa, b) to be used in the present invention can be produced for example in accordance with the procedure of Japanese Patent Application No. 057912/'78 (U.S. Patent Application Ser. No. 36,645 fruited to U.S. Pat. No. 4207324) by the following steps.

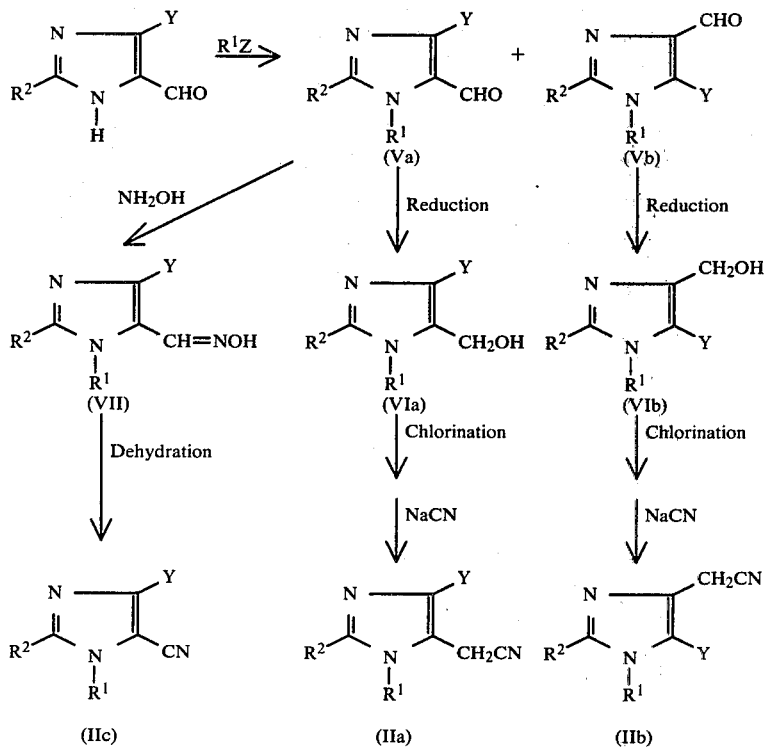

wherein $R^1$ and $R^2$ are as defined hereinbefore; Y and Z are halogen, respectively.

The starting compound (IIc) is produced, for example, in accordance with the procedure as described in "Archiv der Pharmazie", 294, 246 (1961), via the intermediates (Va) through (VII).

The intermediate (VIa, b) can also be produced by the following production steps.

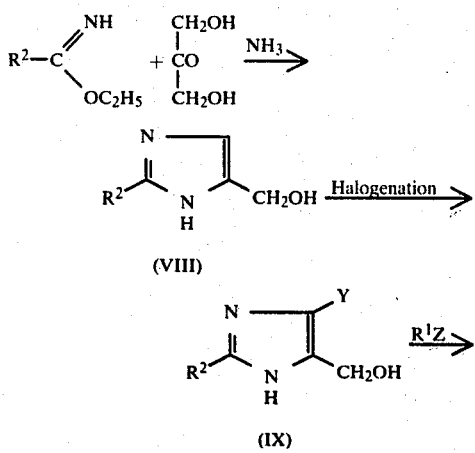

(VIII)

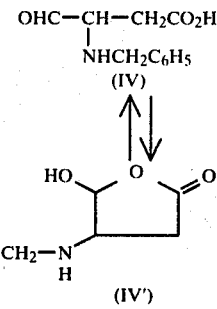

(IX)

wherein each of the symbols are as defined hereinbefore.

The intermediate (VIII) is produced, for example, by the procedure as described in "Archiv der Pharmazie", 307, 470 (1974). The halogenation of the compound (VIII) is conducted by reacting in a solvent such as dioxane and methyl cellosolve at 40° to 100° C. for 1 to 10 hours while using 1 to 2 equivalents of N-halogenosuccinimide. Reaction of the compound (IX) obtained in this manner with alkyl halide or benzyl halide is conducted in a solvent in the presence of acid acceptor. As such acid acceptors are used potassium carbonate, sodium carbonate, sodium hydride, sodium methylate, sodium ethylate, etc., and, in case of the last three, it is recommended to treat with (IX) in advance to form the sodium salt. As preferred examples of the solvent may be mentioned dimethylformamide, dimethylsulfoxide. The reaction is preferably carried out by stirring at about 20° to 100° C. for 1 to 10 hours. Separation of the compounds (VIa) from (VIb) is conducted by the conventional chemical procedures, such as recrystallization and chromatography. The starting compound (IV) utilized in the production of the compound (I') is prepared by the following production steps.

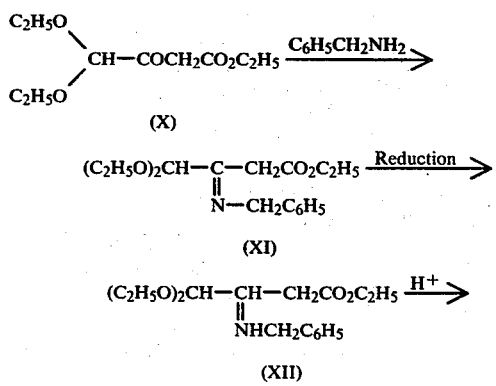

When a nearly equimolar mixture of ethyl γ,γ-diethoxyacetoacetate (X) and benzylamine is boiled in a solvent such as chloroform or benzene for 1 to 5 hours, there results a Schiff base (XI), which is then reduced to ethyl β-benzylamino-γ,γ-diethoxybutyrate (XII). The reduction is preferably done by means of sodium cyanoborohydride or high-pressure catalytic reduction with use of Raney-nickel as a catalyst, whereby methanol, ethanol, etc. are employed as a solvent. As to the reaction conditions, the reaction is desirably conducted at room temperature for 10 to 20 hours in the former case, and at 100° to 150° C. for 5 to 10 hours in the latter. The resulting compound (XII) is hydrolyzed with use of a mineral acid such as hydrochloric acid and sulfuric acid to obtain β-benzylamino-β-formylpropionic acid (IV). The hydrolysis is preferably carried out by heating in an aqueous alcohol at 50° to 100° C. for 1 to 5 hours. The resultant compound (IV) also exists as a tautomeric isomer of the lactone represented by a structural formula (IV').

The present invention is more specifically illustrated in the following Examples, Experiment Examples and Reference Examples; however, it goes without saying that these are not intended to limit the present invention,

EXAMPLE 1

3.2 g of 1-n-butyl-4-chloro-2-phenyl-5-cyanomethylimidazole was heated in 18 ml of 60% sulfuric acid at 145° C. for 15 hours. The reaction solution, under cooling with ice, was made to pH 4 with 20% aqueous sodium hydroxide solution, and the deposited precipitate was recrystallized twice from 50 ml of 60% ethanol, thus yielding 2.4 g of 1-n-butyl-4-chloro-2-phenylimidazole-5-acetic acid as colorless needles, m.p. 189°–190° C.

Elementary analysis, for $C_{15}H_{17}N_2O_2Cl$

| | C (%) | H (%) | N (%) | Cl (%) |
| --- | --- | --- | --- | --- |
| Calcd. | 61.55 | 5.86 | 9.56 | 12.11 |
| Found | 61.44 | 5.73 | 9.71 | 11.98 |

EXAMPLE 2

6.2 g of 4-chloro-2-phenyl-1-phenethyl-5-cyanomethylimidazole was boiled in 62 ml of 6 N-hydrochloric acid for 5 hours. Colorless crystals, which separated out from the reaction solution upon cooling with ice, were dissolved in 50 ml of hot ethanol, and hexane was added little by little to the solution until there developed turbidity. The solution was allowed to cool, and there separated out 4.1 g of 4-chloro-2-phenyl-1-phenethylimidazole-5-acetic acid hydrochloride as colorless needles, m.p. 175°–178° C.

Elementary analysis, for $C_{19}H_{17}N_2O_2Cl.HCl$

|  | C (%) | H (%) | N (%) | Cl (%) |
|---|---|---|---|---|
| Calcd. | 60.49 | 4.81 | 7.42 | 18.79 |
| Found | 60.47 | 4.83 | 7.37 | 18.41 |

EXAMPLES 3 TO 8

In accordance with Examples 2 and 3, there were obtained the following compounds.

TABLE 1

$$R^2 \text{—imidazole with Cl and } (CH_2)_n COOH, N-R^1$$

| Example No. | $R^1$ | $R^2$ | Position of Cl | n | m.p. (°C.) |
|---|---|---|---|---|---|
| 3 | PhCH₂— | Ph— | 5 | 1 | 210–212 (decomp.) |
| 4 | PhCH₂— | Ph— | 4 | 2 | 159–160 |
| 5 | PhCH₂— | n-C₄H₉ | 5 | 1 | 139–141 |
| 6 | (o-Cl)PhCH₂— | n-C₄H₉ | 5 | 1 | 132–133 |
| 7 | PhCH₂— | cyclopentyl | 5 | 1 | 164–165 |
| 8 | PhCH₂— | Ph— | 4 | 0 | 182–183 (decomp.) |

EXAMPLE 9

In 50 ml of ethanol was dissolved 3.5 g of 1-benzyl-4-chloro-2-(4-dimethylaminophenyl)-5-cyanomethylimidazole, and 10 ml of 1 N-sodium hydroxide was added to the solution, followed by stirring at 60° C. for 2 hours. The solution was allowed to cool, and the resulted crystals were recrystallized from 70 ml of 90% ethanol, thereby yielding 2.2 g of 1-benzyl-4-chloro-2-(4-dimethylaminophenyl)imidazole-5-acetamide as colorless needles, m.p. 215°–216° C.

Elementary analysis, for $C_{20}H_{21}N_4OCl$

|  | C (%) | H (%) | N (%) | Cl (%) |
|---|---|---|---|---|
| Calcd. | 65.15 | 5.74 | 15.18 | 9.62 |
| Found | 65.34 | 5.56 | 15.26 | 9.67 |

EXAMPLE 10

In 40 ml of 20% ammonia-methanol was dissolved 1 g of methyl 1-benzyl-4-chloro-2-(4-diethylaminophenyl)imidazole-5-acetate, and the solution was allowed to stand at 30° C. for 50 hours. The reaction solution was evaporated to dryness under reduced pressure, and the residue was dissolved in 30 ml of ether-petroleum ether (1:1). Upon cooling, there separated out 0.4 g of 1-benzyl-4-chloro-2-(4-diethylaminophenyl)imidazole-5-acetamide as slightly brown needles, m.p. 88°–90° C. Elementary analysis, for $C_{22}H_{25}N_4OCl$

|  | C (%) | H (%) | N (%) | Cl (%) |
|---|---|---|---|---|
| Calcd. | 66.55 | 6.35 | 14.11 | 8.94 |
| Found | 66.41 | 6.72 | 13.86 | 8.62 |

EXAMPLES 11 TO 14

In accordance with Examples 9 and 10, there were obtained the following compounds.

TABLE 2

$$R^2 \text{—imidazole with Cl and } (CH_2)_n CONH_2, N-R^1$$

| Example No. | $R^1$ | $R^2$ | n | m.p. (°C.) |
|---|---|---|---|---|
| 11 | PhCH₂— | Ph— | 0 | 169–170 |
| 12 | PhCH₂— | Ph— | 1 | 171–172 (decomp.) |
| 13 | PhCH₂— | (CH₃)₂N—C₆H₄— | 0 | 204–205 |
| 14 | PhCH₂— | n-C₄H₉— | 1 | 121–122 |

EXAMPLE 15

3.1 g of 1-benzyl-5-chloro-2-phenyl-4-cyanomethylimidazole, together with 2.1 g of p-toluenesulfonic acid monohydrate, was boiled in 100 ml of ethanol for 10 hours. The reaction solution was evaporated to dryness under reduced pressure, and the residue was dissolved in 50 ml of chloroform, followed by washing with 50 ml each of a 5% aqueous sodium bicarbonate solution and water to evaporate the chloroform layer to dryness under reduced pressure. The residue was chromatographed on a column of 60 g of silica gel, and eluted with chloroform. The fractions of the objective compound were collected and evaporated to dryness under reduced pressure, followed by dissolving the residue in 2 ml of 20% hydrogen chloride-ethanol. Upon addition of 50 ml of ether, there was obtained 1.5 g of ethyl 1-benzyl-5-chloro-2-phenylimidazole-4-acetate hydrochloride as colorless prisms, m.p. 120°–124° C.

Elementary analysis, for $C_{20}H_{19}N_2O_2Cl.HCl$

|  | C (%) | H (%) | N (%) | Cl (%) |
|---|---|---|---|---|
| Calcd. | 61.55 | 5.17 | 7.18 | 18.16 |
| Found | 61.23 | 5.34 | 6.85 | 18.31 |

EXAMPLE 16

2 g of ethyl benzimidate and 3 g of β-benzylamino-β-formylpropionic acid were boiled in a mixed solution of 30 ml of dioxane and 10 ml of ethanol at 110° C. for 2 hours. The reaction solution was evaporated to dryness under reduced pressure, and 50 ml each of chloroform and water were added to the residue, followed by shaking to extract the chloroform layer again with water. The water layers were combined, concentrated to about 20 ml and made to pH 4.5 with sodium bicarbonate. When the solution was allowed to cool, there separated out 2.1 g of 1-benzyl-2-phenylimidazole-5-acetic acid as colorless needles, m.p. 87°–90° C.

Elementary analysis, for $C_{18}H_{16}N_2O_2$

|  | C (%) | H (%) | N (%) |
|---|---|---|---|
| Calcd. | 73.95 | 5.52 | 9.58 |
| Found | 73.87 | 5.61 | 9.48 |

EXAMPLES 17 TO 20

In accordance with Example 16, there were obtained the following compounds.

TABLE 3

[Structure: imidazole with R² substituent, N-CH₂-phenyl group, and CH₂CO₂H group]

| Example No. | R² | m.p. (°C.) |
|---|---|---|
| 17 | (CH₃)₂N—⟨phenyl⟩— | 110–113 |
| 18 | Cl—⟨phenyl⟩— | 230–232 (decomp.) |
| 19 | CH₃O—⟨phenyl⟩— | 206–208 (decomp.) |
| 20 | CH₃—⟨phenyl⟩— | 213–214 |

EXAMPLE 21

In 200 ml of methanol was dissolved 2.4 g of 1-benzyl-2-phenylimidazole-5-acetic acid monohydrate, and 1 ml of concentrated sulfuric acid was added to the solution. The mixture was boiled for 4 hours. The reaction solution was evaporated to dryness under reduced pressure, and 50 ml of water containing 3.4 g of sodium bicarbonate and 50 ml of chloroform were added to the residue for shaking. The chloroform layer was washed with water and evaporated to dryness under reduced pressure. The residue was dissolved in a small amount of ether, and hexane was added to the solution, thereby yielding 2 g of methyl 1-benzyl-2-phenylimidazole-5-acetate as colorless crystals, m.p. 78°–79° C.

Elementary analysis, for $C_{19}H_{18}N_2O_2$

|  | C (%) | H (%) | N (%) |
|---|---|---|---|
| Calcd. | 74.49 | 5.92 | 9.15 |
| Found | 74.45 | 6.16 | 9.11 |

EXAMPLE 22

In 20 ml of glacial acetic acid was dissolved 1.2 g of methyl 1-benzyl-2-phenylimidazole-5-acetate, and 20 ml of fuming nitric acid (specific gravity of 1.52) was added to the solution, followed by stirring at room temperature for 2 hours. The reaction solution was poured into 1 l of ice water, neutralized with sodium bicarbonate, and extracted with three 100 ml portions of ethyl acetate. The ethyl acetate layers were combined and evaporated to dryness under reduced pressure, followed by chromatographing on a column of 50 g of silica gel to thereby elute with benzene-ethyl acetate (1:1). The fractions of the objective compound were collected and evaporated to dryness under reduced pressure, yielding 1.25 g of methyl 1-(4-nitrobenzyl)-2-phenylimidazole-5-acetate as colorless crystals. Recrystallization of a part of the compound from benzene-hexane afforded the crystals, m.p. 113°–116° C.

Elementary analysis, for $C_{19}H_{17}N_3O_4$

|  | C (%) | H (%) | Cl (%) |
|---|---|---|---|
| Calcd. | 64.95 | 4.88 | 11.96 |
| Found. | 65.23 | 4.86 | 11.91 |

EXAMPLE 23

In 5 ml of ethanol was dissolved 330 mg of 1-benzyl-5-chloro-2-phenylimidazole-4-acetic acid, and a solution of 40 mg of sodium hydroxide in 1 ml of water was added to the solution. The mixed solution was evaporated to dryness under reduced pressure, and the residue was dissolved in 2 ml of ethanol. Upon addition of 20 ml of ether, there was obtained 0.3 g of sodium salt of the above-mentioned compound as colorless, crystalline powder, m.p. 290°–300° C. (decomp.).

In accordance with Examples 1 to 23, the following compounds are able to be prepared.

1-Benzyl-4-bromo-2-phenylimidazole-5-acetamide;
1-(2-Nitrobenzyl)-5-chloro-2-butylimidazole-4-acetic acid; and
1-(2-Ethoxybenzyl)-5-chloro-2-butylimidazole-4-acetic acid.

EXAMPLE 24

In cases in which the compound (I) of the present invention is employed for example as a treatment agent for essential hypertension, it can be used for example by the following formulations:

1. Tablets

| (1) 1-Benzyl-2-butyl-5-chloroimidazole-4-acetic acid | 10 mg |
|---|---|
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2), (3) and two thirds of (4) were mixed with a half of (5), and granulated. The remainders of (4) and (5) were added to the granules and pressed into a tablet.

| 2. Capsules | |
|---|---|
| (1) 1-Benzyl-2-butyl-4-chloroimidazole-5-acetamide | 10 mg |
| (2) Lactose | 90 mg |
| (3) Microcrystalline cellulose | 70 mg |
| (4) Magnesium stearate | 5 mg |
| One capsule | 190 mg |

(1), (2) and (3) were mixed with one half of (4), and granulated. The remainder of (4) was added to the mixture to fill the whole into a gelatin capsule.

| 3. Injections | |
|---|---|
| (1) Sodium 1-benzyl-5-chloro-2-phenylimidazole-4-acetate | 10 mg |
| (2) Inosite | 100 mg |
| (3) Benzyl alcohol | 20 mg |
| One ampoule | 130 mg |

(1), (2) and (3) were dissolved in ditilled water for injection to make 2 ml of the whole solution, and filled in an ampoule. The whole preparation process was conducted in the sterile condition.

REFERENCE EXAMPLE 1

In 22 ml of chloroform was dissolved 3.97 g of 1-butyl-4-chloro-2-phenyl-5-hydroxymethylimidazole, and 2.18 ml of thionyl chloride was added little by little to the solution, followed by allowing it to stand at room temperature for 2 hours. The reaction solution was evaporated to dryness under reduced pressure, and 30 ml of toluene was added to the residue. The mixture was evaporated to dryness under reduced pressure. The residue was dissolved in 15 ml of dimethylsulfoxide, and the solution was added dropwise to a suspension of 3.68 g of sodium cyanide in dimethylsulfoxide with vigorous stirring. After the addition, the reaction solution was stirred at room temperature for 2 hours and poured into 200 ml of water to extract with two 100 ml portions of chloroform. The chloroform layer was evaporated to dryness under reduced pressure, and the residue was chromatographed on a column of 80 g of silica gel, followed by eluting with chloroform. The fractions of the objective compound were collected and evaporated to dryness under reduced pressure, thus yielding 3.2 g of 1-butyl-4-chloro-2-phenyl-5-cyanomethylimidazole as a colorless, resinous substance. Infrared absorption spectrum (film): 2250 cm$^{-1}$ (CN)

REFERENCE EXAMPLES 2 TO 10

In accordance with Reference Example 1, there were obtained the following compounds.

TABLE 4

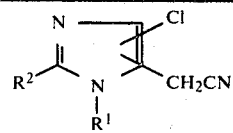

| Reference Example No. | R$^1$ | R$^2$ | Position of Cl | m.p. (°C.) |
|---|---|---|---|---|
| 2 | phenyl-CH$_2$CH$_2$— | phenyl- | 4 | resinous |
| 3 | phenyl-CH$_2$— | phenyl- | 5 | 110-112 |
| 4 | phenyl-CH$_2$— | n-C$_4$H$_9$- | 5 | resinous |
| 5 | (2-Cl-phenyl)-CH$_2$— | n-C$_4$H$_9$— | 5 | 68-69 |
| 6 | phenyl-CH$_2$— | cyclobutyl- | 5 | resinous |
| 7 | phenyl-CH$_2$— | phenyl- | 4 | 121-122 |
| 8 | phenyl-CH$_2$— | (CH$_3$)$_2$N-phenyl- | 4 | 147-149 |
| 9 | phenyl-CH$_2$— | (C$_2$H$_5$)$_2$N-phenyl- | 4 | 125-127 |
| 10 | phenyl-CH$_2$— | n-C$_4$H$_9$— | 4 | 122-123 (hydrochloride) |

REFERENCE EXAMPLE 11

In 30 ml of pyridine were dissolved 3.4 g of 1-benzyl-4-chloro-2-(4-dimethylaminophenyl)-5-formylimidazole and 1.39 g of hydroxylamine hydrochloride, and 6 ml of acetic anhydride was added dropwise to the solution. After the addition was completed, the reaction solution was stirred at 100° C. for 3 hours, and evaporated to dryness under reduced pressure. The residue was dissolved in 100 ml of chloroform, washed with two 300 ml portions of water, and evaporated to dryness under reduced pressure. The residue was recrystallized twice from 30 ml of ethanol, yielding 2.1 g of 1-benzyl-4-chloro-2-(4-dimethylaminophenyl)-5-cyanoimidazole as slightly brown needles, m.p. 125°-127° C.

Infrared absorption spectrum (KBr): 2200 cm$^{-1}$ (CN).

REFERENCE EXAMPLE 12

In a mixture of 70 ml of dioxane and 60 ml of methyl cellosolve was dissolved 4 g of 2-butyl-5-hydroxymethylimidazole, and 3.9 g of N-chlorosuccinimide was added to the solution, followed by stirring at 40° C. for 1 hour. The reaction solution was evaporated to dryness under reduced pressure, and 100 ml each of water and ethyl acetate were added to the residue to shake for mixing. The ethyl acetate layer was evaporated to dryness under reduced pressure, and the residue was dissolved in 50 ml of ether. The solution was allowed to cool, thereby yielding 2.4 g of 2-butyl-4-chloro-5-hydroxymethylimidazole deposited as colorless prisms, m.p. 147°–148° C.

Elementary analysis, for $C_8H_{13}N_2OCl$

|  | C (%) | H (%) | N (%) |
|---|---|---|---|
| Calcd. | 50.93 | 6.95 | 14.85 |
| Found | 50.70 | 6.85 | 14.92 |

3.93 g of 2-butyl-4-chloro-5-hydroxymethylimidazole was dissolved in 50 ml of methanol, and the solution was added to 10 ml of methanol solution of 479 mg of sodium, followed by evaporating the mixture to dryness under reduced pressure. The residue was dissolved in 20 ml of dimethylformamide, and 3.92 g of benzyl bromide was added to the solution to stir at 30° to 40° C. for 2 hours. The reaction solution was poured in 500 ml of water to extract with 300 ml of ethyl acetate. The ethyl acetate layer was evaporated to dryness under reduced pressure, and chromatographed on a column of 200 g of silica gel, followed by eluting with ethyl acetate-benzene (1:3). While the first fraction yielded 1.4 g of 1-benzyl-2-butyl-4-chloro-5-hydroxymethylimidazole, the second fraction was collected and evaporated to dryness under reduced pressure, and addition of 30 ml of ether to the residue, followed by allowing the mixture to cool, afforded 1.3 g of 1-benzyl-2-butyl-5-chloro-4-hydroxymethylimidazole as colorless prisms, m.p. 78°–80° C.

Elementary analysis, for $C_{15}H_{19}N_2OCl$

|  | C (%) | H (%) | N (%) |
|---|---|---|---|
| Calcd. | 64.63 | 6.87 | 10.05 |
| Found | 64.90 | 6.87 | 9.99 |

REFERENCE EXAMPLE 13

79 g of ethyl γ,γ-diethoxyacetoacetate and 40 ml of benzylamine were boiled in 300 ml of benzene for 1 hour. The reaction solution, after distilling off benzene, was distilled under reduced pressure, thus yielding 102 g of the corresponding Schiff base as a colorless liquid, b.p. 147°–149° C./0.3–0.4 mmHg.

30 g of the product was dissolved in 200 ml of ethanol, to which 17.5 ml of 20% hydrogen chloride-ethanol and then 9 g of sodium cyanoborohydride were added at 0° C. little by little. After the additions were completed, the reaction solution was stirred at room temperature for 15 hours and evaporated to dryness under reduced pressure. The residue was dissolved in 300 ml of ether and washed with water. The ether layer was evaporated to dryness under reduced pressure, yielding 27 g of ethyl γ,γ-diethoxy-β-benzylaminobutyrate as a slightly yellow liquid.

9.9 g of the product was subjected to the reaction in a mixture of 35 ml each of ethanol, water and concentrated hydrochloric acid at 80° C. for 2 hours. The mixture was evaporated to dryness under reduced pressure, and 50 ml of toluene was added to the residue, followed by evaporating again to dryness under reduced pressure. The residue was dissolved in 30 ml of acetone and allowed to cool, thereby yielding 4.4 g of β-benzyl-amino-β-formylpropionic acid hydrochloride deposited as colorless prisms, m.p. 125°–130° C. (decomp.).

Elementary analysis, for $C_{11}H_{13}NO_3 \cdot HCl$

|  | C (%) | H (%) | N (%) |
|---|---|---|---|
| Calcd. | 54.22 | 5.79 | 5.75 |
| Found | 54.55 | 5.67 | 5.89 |

EXPERIMENT EXAMPLE 1

Angiotensin II (hereinafter referred to briefly as A II) antagonistic effect of the compound (I) of the present invention (aortic blood vessel of a rabbit).

The blood-vessel preparation and reaction were done in accordance with the method as described in "European Journal of Pharmacology", vol. 18, pp. 316 (1972). While employing A II in the concentration of $4 \times 10^{-9}M$, the potency of inhibition was calculated by the following equation from changes in isometric tension of the blood vessel brought about by A II and that found after treatment with a test drug substance for 15 minutes, respectively.

$$\text{Potency of inhibition (\%)} = \frac{T_1 - T_2}{T_1} \times 100$$

where;
$T_1$ = Change in isometric tension of the blood vessel brought about by A II without treatment with a test drug substance (g)
$T_2$ = Change in tension found after treatment with a test drug substance (g)

The results are shown in Table 5.

TABLE 5

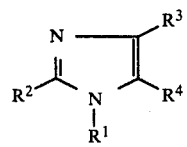

| compound | | | | Concn. of drug | Potency of |
|---|---|---|---|---|---|
| $R^1$ | $R^2$ | $R^3$ | $R^4$ | substance (M) | inhibition (%) |
| ⌬-CH₂— | ⌬— | —CH₂CO₂H | Cl | $10^{-5}$ | 10 |

TABLE 5-continued $$\begin{array}{c} R^3 \\ N \longrightarrow \\ R^2 \underset{\underset{R^1}{|}}{\overset{\|}{N}} R^4 \end{array}$$

| compound | | | | Concn. of drug substance (M) | Potency of inhibition (%) |
|---|---|---|---|---|---|
| $R^1$ | $R^2$ | $R^3$ | $R^4$ | | |
| PhCH$_2$— | Ph— | Cl | —CO$_2$H | $10^{-5}$ | 5 |
| PhCH$_2$— | Ph— | Cl | —(CH$_2$)$_2$CO$_2$H | $10^{-5}$ | 13 |
| n-C$_4$H$_9$— | Ph— | Cl | —CH$_2$CO$_2$H | $10^{-5}$ | 25 |
| PhCH$_2$CH$_2$— | Ph— | Cl | —CH$_2$CO$_2$H | $10^{-5}$ | 12 |
| PhCH$_2$— | n-C$_4$H$_9$— | —CH$_2$CO$_2$H | Cl | $10^{-6}$ | 22 |
| PhCH$_2$— | cyclopentyl | —CH$_2$CO$_2$H | Cl | $10^{-6}$ | 10 |
| O$_2$N—C$_6$H$_4$—CH$_2$— | Ph— | H | —CH$_2$CO$_2$CH$_3$ | $10^{-5}$ | 38 |
| PhCH$_2$— | Ph— | Cl | —CH$_2$CONH$_2$ | $10^{-5}$ | 20 |
| PhCH$_2$— | (CH$_3$)$_2$N—C$_6$H$_4$— | Cl | —CH$_2$CONH$_2$ | $10^{-5}$ | 10 |
| PhCH$_2$— | (CH$_3$)$_2$N—C$_6$H$_4$— | Cl | —CONH$_2$ | $10^{-5}$ | 18 |
| PhCH$_2$— | n-C$_4$H$_9$— | Cl | —CH$_2$CONH$_2$ | $10^{-6}$ | 19 |
| PhCH$_2$— | CH$_3$—C$_6$H$_4$— | H | —CH$_2$CO$_2$H | $10^{-5}$ | 5 |
| PhCH$_2$— | CH$_3$O—C$_6$H$_4$— | H | —CH$_2$CO$_2$H | $10^{-5}$ | 5 |
| 2-Cl-C$_6$H$_4$-CH$_2$— | n-C$_4$H$_9$— | —CH$_2$CO$_2$H | Cl | $10^{-6}$ | 30 |

What is claimed is
1. (6) A compound of the formula:

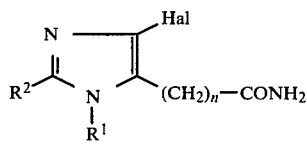

wherein
R$^1$ is lower alkyl, or phenyl-C$_{1-2}$alkyl which may be substituted with halogen or nitro;
R$^2$ is lower alkyl, lower cycloalkyl, or phenyl which may be substituted with halogen, lower alkyl, lower alkoxyl or di(lower alkyl)amino,
Hal is halogen and
n is 0, 1 or 2;
or a pharmaceutically acceptable salt thereof.
2. A compound according to claim 1, wherein n is 1.

3. A compound according to claim 1, which is 1-benzyl-4-chloro-2-phenylimidazole-5-acetamide.

4. A compound according to claim 1, which is 1-benzyl-2-n-butyl-4-chloroimidazole-5-acetamide.

5. A compound of the formula:

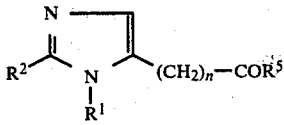

wherein
R¹ is benzyl which may be substituted with halogen or nitro;
R² is lower alkyl, lower cycloalkyl, or phenyl which may be substituted with halogen, lower alkyl, lower alkoxyl or di(lower alkyl)amino,
R⁵ is amino, lower alkoxyl or hydroxyl, and
n is 0, 1 or 2;
or a pharmaceutically acceptable salt thereof.

6. A compound according to claim 5, wherein n is 1.

7. A compound according to claim 5, which is methyl 1-(4-nitrobenzyl)-2-phenylimidazole-5-acetate.

8. A compound of the formula:

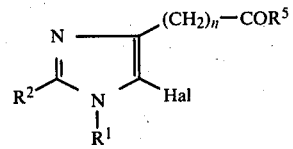

wherein
R¹ is lower alkyl, or phenyl-$C_{1-2}$alkyl which may be substituted with halogen or nitro;
R² is lower alkyl,
R⁵ is amino, lower alkoxyl or hydroxyl,
Hal is halogen, and
n is 0, 1 or 2.

9. A compound according to claim 8, wherein R⁵ is hydroxyl.

10. A compound according to claim 8, which is 1-benzyl-2-n-butyl-5-chloroimidazole-4-acetic acid.

11. A pharmaceutical composition useful for treating hypertension which contains an amount effective for producing hypotensive activity in a mammal of a compound claimed in claim 2, 3, 5, 6, 8, 9, or 10 and a pharmaceutically acceptable carrier, vehicle or diluent therefor.

12. A method for producing hypotensive activity in a mammal, which comprises administering to said mammal a hypotensively effective amount of a compound of claim 2, 3, 5, 6, 8, 9 or 10.

* * * * *